United States Patent [19]
Nappa et al.

[11] Patent Number: 5,770,779
[45] Date of Patent: Jun. 23, 1998

[54] PROCESS FOR PREPARATION OF FLUORINATED HYDROCARBONS

[75] Inventors: Mario Joseph Nappa, Newark, Del.; William Robert Williams, New Fairfield, Conn.

[73] Assignee: E. I. du Pont de Nemours and Company, Wilmington, Del.

[21] Appl. No.: 778,427

[22] Filed: Jan. 2, 1997

[51] Int. Cl.[6] .................................................. C07C 17/08
[52] U.S. Cl. ........................................... 570/166; 570/168
[58] Field of Search ..................................... 570/168, 166

[56] References Cited

U.S. PATENT DOCUMENTS

| | | | |
|---|---|---|---|
| 3,536,769 | 10/1970 | Shigeru Seki et al. | 260/653.6 |
| 4,766,258 | 8/1988 | Komatsu et al. | 570/168 |
| 4,968,850 | 11/1990 | Franklin et al. | 570/166 |

OTHER PUBLICATIONS

Pazderskii, Yu. A. et al., Ethyl Fluoride, *Chemical Abstract*, vol. 87, No. 21, p. 531 "Abstract", 1977.

*Primary Examiner*—Gary Geist
*Assistant Examiner*—Sreeni Padmanabhan
*Attorney, Agent, or Firm*—James E. Shipley

[57] ABSTRACT

This invention is a process for the selective preparation of fluorinated hydrocarbons from chlorinated hydrocarbons while minimizing formation of oligomeric and polymeric byproducts. The process comprises providing a liquid phase containing chlorinated hydrocarbon, HF, a tin catalyst, and at least one compound selected from the group consisting of metal and nonmetal alkoxides, and heating the mixture and isolating the fluorinated hydrocarbon formed.

10 Claims, 1 Drawing Sheet

PROCESS FOR PREPARATION OF FLUORINATED HYDROCARBONS

This application is a continuation of Provisional Application Ser. No. 60/009,668, dated Jan. 5, 1996.

FIELD OF THE INVENTION

The present invention relates to processes for selective and high yield preparation of fluorinated hydrocarbons and more particularly to such processes which comprise contacting a chlorinated hydrocarbon with hydrogen fluoride in a liquid phase in the presence of a tin catalyst and a metal or nonmetal alkoxide additive.

BACKGROUND OF THE INVENTION

Franklin et al., in U.S. Pat. No. 4,968,850, disclose a process for the preparation of hydrofluorocarbons (HFCs) and hydrochlorofluorocarbons (HCFCs) by allowing an unsaturated hydrochlorocarbon (HCC) to react with hydrogen fluoride (HF) in a liquid phase in the presence of a tin catalyst and an organophosphorous additive. These additives are described to lead to an efficient halogen exchange process in which the activity of the catalyst used is increased and/or the stability of the additives is improved, and in which few oligomers are formed and the selectivity for worthwhile products is high. However, while exhibiting a decrease in the amount of oligomers formed, the examples reveal a process in which the selectivity for formation of higher fluorinated hydrocarbons is decreased or changed in a negligible manner.

Komatsu et al., in U.S. Pat. No. 4,766,258, disclose a process for the manufacture of HFCs and HCFCs by allowing HCCs to react with HF in the presence of a tin catalyst and an additive chosen from compounds containing oxygen or nitrogen. In most cases, the examples reveal that the additives reduce the activity of the tin catalyst and thus compromise the efficiency of this process towards forming useful yields of higher fluorinated hydrocarbons.

Komatsu et al., in Japanese Kokai publication number SHO 62[1987]-246528, disclose a process for manufacture of HFCs and HCFCs, characterized by allowing a hydrogen-containing halogenated hydrocarbon to react with HF in a liquid phase in the presence of the reaction product from a compound acting as a base in HF, a tin catalyst, and HF. Komatsu teaches the invention in a single example where 1,1,2-trichloroethane is allowed to react with HF in the presence of tin tetrachloride and sodium fluoride. The reaction was carried out as a batch process at 90° to 98° C. and 980 kPa for three hours, and the charged mole ratio of reactants was 1,1,2-trichloroethane (16.7): HF (33.3): $SnCl_4$ (1.0): NaF (1.0). In this example, the isolated product mixture was 32% (wt) 1,2-dichloro-1-fluoroethane (HCFC-141), 1% 1-chloro- 1,2-difluoroethane (HCFC-142a), and 67% recovered starting material (1,1,2- trichloroethane) with no dimers observed. Based on this single example, all additives disclosed in this Kokai publication, used in a process otherwise identical to U.S. Pat. No. 4,766,258 issued to these same authors, are proposed to provide similar benefits.

HFCs are of current interest and may be used either alone or in blends with other materials as refrigerants, blowing agents, propellants, cleaning agents, or as intermediates in preparation of other fluorinated hydrocarbons. HFCs such as 1,1-difluoroethane (HFC-152a) and 1,1,1-trifluoroethane (HFC-143a), are environmentally acceptable replacements for chlorofluorocarbons (CFCs), since they have no known adverse effect upon the earth's stratospheric ozone.

Processes for preparing HFCs and HCFCs from HCCs and HF by metal mediated halogen exchange have found wide industrial utility. The overall process is one in which carbon to chlorine bonds of the HCC are broken and carbon to fluorine bonds are formed in their place. The metal acts in a catalytic capacity leading to a more productive exchange process requiring milder reaction conditions. A wide variety of HFCs and HCFCs have been manufactured in this manner using liquid or gas phase processes. Fluorinated hydrocarbons of vast utility such as 1,1,1,2-tetrafluoroethane (HFC-134a), HFC-143a, 1-chloro-1,1-difluoroethane (HCFC-142b), HFC-152a, and 1,1-dichloro-2,2,2-trifluoroethane (HCFC-123 ) have been prepared in the art by allowing an appropriate chlorinated hydrocarbon to react with HF in the presence of salts of various oxidized metals. Salts of metal species such as tin(IV), titanium(IV), antimony(III), and antimony(V) have been found to lead to productive halogen exchange processes. Application of such processes involving these metal species and HF for preparation of HFCs and HCFCs has led to varied degrees of success in the art. More often than not in the preparation of higher fluorinated hydrocarbons, these procedures are disfavored because of incomplete fluorination of the chlorinated hydrocarbon and complications and low yields due to formation of undesirable oligomeric and polymeric byproducts.

Byproducts of such conventional procedures include an assortment of oligomeric and polymeric materials; low molecular weight halogenated dimers and oligomers through higher molecular weight halogenated polymers taking the form of oils, tars and dark carbonaceous solids. These byproducts are typically higher molecular weight, e.g., predominately 50,000, with standard weight fraction distribution from 2,000 to 75,000 number averaged molecular weight, branched, polymeric, halogenated hydrocarbons, which may contain metal species acquired from catalyst and other additives, if present. Such higher molecular weight materials can be formed by polymerization of lower molecular weight dimers, trimers, and oligomers with themselves or with the halogenated carbon-containing reagents and their fluorinated adducts. These byproducts are detrimental to the halogen exchange process as they interfere with the catalyst activity, reduce reactor volume, and decrease the yield of fluorinated hydrocarbon as well as create concerns and expenses around such issues as separation, waste treatment and disposal, and apparatus downtime.

Modification of a tin catalyst by addition of compounds which are inert to fluorination but reactive with the tin(IV) species in HF, leads to tin catalysts with different properties from the parent. The ideal additive for the exchange process is one which minimizes byproduct formation while enhancing the reaction rate and selectivity towards the desired product.

Conventional processes for making fluorinated hydrocarbons such as HFC-152a and HFC-143a from chlorinated hydrocarbons such as chloroethene and 1,1-dichloroethene are undesirable due to the high amounts of tars produced. The inventive process solves the problems associated with conventional processes by reducing the tar formation rates.

SUMMARY OF THE INVENTION

This invention is a process for the selective preparation of fluorinated hydrocarbons from chlorinated hydrocarbons while minimizing formation of oligomeric and polymeric byproducts. The process comprises: providing a liquid phase mixture containing chlorinated hydrocarbon, HF, at least one tin catalyst, and at least one compound from the group consisting of metal and non-metal alkoxides; heating the mixture; and isolating the fluorinated hydrocarbon formed.

The reaction components may be charged to a reaction vessel in any order, but preferably, the vessel is first charged with tin catalyst, HF, and the metal or non-metal alkoxide. The temperature of this mixture is maintained from about 20° to 160° C. over the reaction period. During this period, chlorinated hydrocarbon is added and is converted to fluorinated hydrocarbon under the reaction conditions.

The process of the present invention can be operated as a batch process. It is preferable to operate a continuous process by the continuous addition of HF, tin catalyst, and metal or non-metal alkoxide to the reaction vessel along with chlorinated hydrocarbon, accompanied by the removal of fluorinated hydrocarbon and HCl. Analysis of this process reveals high and selective conversion of chlorinated hydrocarbon to fluorinated hydrocarbon while minimizing the amounts of oligomeric and polymeric byproducts.

DETAILED DESCRIPTION OF THE INVENTION

Figure 1:
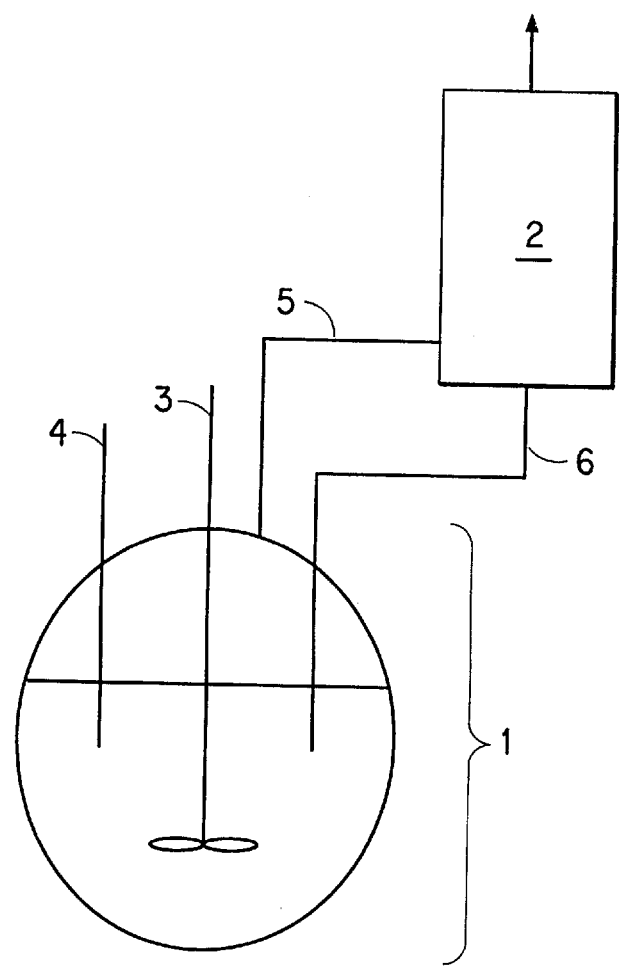
FIG. 1—Schematic of the continuous process used to produce fluorinated hydrocarbons.

This invention is a process for the selective and high yield synthesis of fluorinated hydrocarbons from chlorinated hydrocarbons while minimizing the formation of byproducts. The process comprises: providing a liquid mixture comprising HF, at least one chlorinated hydrocarbon, at least one tin catalyst, and at least one compound selected from the group consisting of a metal and a nonmetal alkoxide; heating the mixture; and isolating the fluorinated hydrocarbon formed substantially free of oligomeric and polymeric compounds, i.e., less than about 0.5 g per 100 g of chlorinated hydrocarbon fed.

The process has been found to benefit greatly when the metal or nonmetal alkoxide employed is a tetraalkyl borate, such as triethyl borate ($B(OC_2H_5)_3$), or a tetraalkyl orthosilicates such as tetraethyl orthosilicate ($Si(OC_2H_5)_4$). As shown by Example 1 of this work, employing triethyl borate in a process involving synthesis of HFC-152a from chloroethene leads to a 3.3-fold increase in the molar selectivity of HFC-152a/HCFC-151a and a 2.3 fold decrease in the weight of tars formed over a comparative process in which no borate additive is used. Example 4 of this work shows that using tetraethyl orthosilicate in the process involving synthesis of HFC143a from 1,1,1-trichloroethane, leads to a 5.4-fold increase in the molar selectivity of HFC-143a/HCFC-142b with no change in the rate of tar formation over a comparative process in which no silicate additive is used. It has also been discovered for these processes employing metal and nonmetal alkoxides that similar benefits arise when fluorinated hydrocarbons are co-produced by feeding a mixture of chlorinated hydrocarbons. The synergy of increased product selectivity and increased yield (decreased tar formation), together with the possibility of employing a wide variety of metal or nonmetal alkoxide additives, leads to a valuable process.

Tin catalysts for use in the process of the present invention may be selected from the families of tin halides, tin oxyhalides, and organotins. Of the three families, the tin halides are preferred, and of the tin halides, tin(IV) chloride ($SnCl_4$, stannic chloride) is most preferred. Other acceptable tin(IV) halides include $SnBr_4$ and the series of $SnCl_3F$, $SnCl_2F_2$, $SnClF_3$, and $SnF_4$; such species as are generated when $SnCl_4$ is allowed to react with HF. Of the tin oxyhalides, compounds such as $SnCl_2O$, $SnF_2O$, and $SnClFO$ are acceptable. For the purpose of the present invention, organotins are compounds in which the tin atom is bonded to from one to four carbon atoms. Organotin compounds such as tetramethyl tin ($Sn(CH_3)_4$), oxydiethyl tin ($OSn(C_2H_5)_2$), and dichlorodimethyl tin ($SnCl_2(CH_3)_2$) are useful in the process.

Metal and nonmetal alkoxide additives for use in the process of the present invention are of the general empirical formula $M(OR)_x$, where R is $C_1$ through $C_6$ linear or branched chain alkyl, x is 1–4, and M is selected from the families of metals and nonmetals of the Periodic Table. The metals of the present invention comprise the light metals of groups IA and IIA excluding hydrogen (where group pertains to specified group of a standard periodic table of the elements, such as that represented upon the inner front cover of "Lang's Handbook of Chemistry", Fourteenth Edition, John A. Dean editor, McGraw Hill, Inc., 1992 ), the transition metals of groups IB, IIB, IIIB, IVB, VB, VIB, and VIIIB, and the posttransition metals of groups IIIA, IVA, VA, and VIA, excluding phosphorous. Such metal and nonmetal alkoxide additives may be employed in the process of the present invention alone or in any composition or mixture. Preferred metals are Li, Na, K, Rb, Cs, Be, Mg, Ca, Sr, Ba, Ti, B, Sl, Si, Ge, Sn and Pb. B and Si are most preferred.

Preferred are the posttransition metals boron and silicon. The preferred boron-containing alkoxides of the present invention are from boron-containing organic compounds such as the trialkyl borates $B(OR)_3$, wherein each R is independently a $C_1$ through $C_6$ linear or branched chain alkyl. The preferred silicon-containing alkoxides of the present invention are from tetraalkyl orthosilicates $Si(OR)_4$, wherein each R is independently a $C_1$ through $C_6$ linear or branched chain alkyl. R is preferably the same and is $C_1$–$C_4$ alkyl, most preferably $C_1$–$C_2$ alkyl.

The quantity of boron-containing alkoxide for use in the process of the present invention is generally between 0.05 and 0.6 mole per mole of tin catalyst employed. Preferably, the process employs between 0.05 and 0.5 mole boron-containing alkoxide per mole of tin catalyst. The quantity of silicon-containing alkoxide for use in the process of the present invention is generally between 0.05 and 0.4 mole per mole of tin catalyst used. Preferably, the process employs between 0.05 and 0.35 mole silicon-containing alkoxide per mole of tin catalyst. Generally, the quantity of metal or nonmetal alkoxide additive employed in the process of the present invention is between 0.1/x and 2.0/x mole metal or nonmetal alkoxide per mole of tin catalyst, wherein x is the number of alkoxide groups (—OR) per metal atom, i.e. $M(OR)_x$. Preferably, the process of the present invention employs between 0.5/x and 1.2/x mole metal or nonmetal alkoxide per mole of tin catalyst, wherein x is the number of alkoxide groups per metal or nonmetal atom (M). In general, the mole ratio of additive to tin catalyst will not exceed 1 to 1 be not less than about 0.025 to 1.

Chlorinated hydrocarbons useful in the present invention are selected from the general families of $R^1R^2C=CR^3R^4$ and $CR^5R^6R^7R^8$, wherein at least one of $R^1$ through $R^4$ in $R^1R^2C=CR^3R^4$, and at least one of $R^5$ through $R^8$ in $CR^5R^6R^7R^8$ is chlorine, and wherein the remainder of $R^1$ through $R^8$ groups are independently or together composed of H, F, Cl, Br, or $C_{(y)}Z_{(2y+1)}$, wherein Z is independently or together H, F, Cl or Br, and y is an integer from 1 to 6. Preferred chlorinated hydrocarbons useful in the present invention are chloroethene ($CH_2=CHCl_2$), 1,1- dichloroethene ($CH_2=CCl_2$), tetrachloroethylene ($CCl_2=CCl_2$), 1,1,1-trichloroethane ($CCl_3—CH_3$), 1,1,2-trichloroethane ($CHCl_2-CH_2Cl$), and 1,1,1,3,3,3-hexachloropropane ($CCl_3—CH_2—Cl_3$).

In one aspect of the present invention, the process is performed in a batch operation. Any suitable autoclave, such as a 450 cc Parr® Series 4560 Mini Reactor constructed of Hastelloy C® can be used. The autoclave is typically fitted with a turbine impeller for agitating the liquid contents of the autoclave, a septum port for introducing or withdrawing liquids from the autoclave by syringe or cannula technique, valved ports for introducing or withdrawing gaseous or liquid materials, a jacketed 0.25 inch diameter tube reflux condenser topped with a valved takeoff port, and an external heating jacket. The inventive batch method generally can be carried out on any scale desired. The equipment and associated feed lines, effluent lines, and associated units should be constructed of materials resistant to HF and HCl. Typical materials of construction, well-known to the fluorination art, include stainless steels and high nickel alloys, such as Monel® nickel-copper alloys, Hastelloy® nickel-based alloys, and Inconel® nickel-chromium alloys.

A dry autoclave is transferred into a dry-box and the desired amount of at least one tin catalyst and at least one compound selected from the group consisting of metal and nonmetal alkoxides are charged to the autoclave. These materials are necessarily loaded into the autoclave by any procedure which will minimize contact with moisture present in the air, i.e., standard drybox procedure.

The autoclave is sealed, and removed from the drybox. A port of the autoclave is then attached to a vacuum pump and the lower portion cooled by liquid nitrogen, and the autoclave is evacuated. By establishing a vacuum in the autoclave, potentially deleterious air is removed thereby permitting more efficient transfer of gaseous HF. Liquid nitrogen facilitates transfer of HF by condensing gaseous HF in the autoclave. The autoclave is then attached to an HF cylinder and the desired amount of HF is vacuum transferred into the autoclave.

The quantities of chlorinated hydrocarbon, HF, and tin catalyst present in the autoclave may vary over a broad range of effective operation. The quantity of materials used in the process of the present invention is generally between about 0.1 to at least about 10 (kg chlorinated hydrocarbon fed/hour)/kg tin catalyst, usually about 0.2 (kg chlorinated hydrocarbon fed/hour)/kg tin catalyst when the tin catalyst comprises $SnCl_4$. The initial amount of tin catalyst charged with HF is generally between about 5 to at least about 35 weight %, for example, $SnCl_4$ in HF, normally from about 10 to about 20 weight % tin catalyst in HF.

After the starting materials are introduced into the sealed autoclave, the autoclave is then detached from the vacuum and HF sources, and allowed to warm to ambient temperature. The autoclave is then heated to a temperature of about 20° to about 160° C., preferably from about 50° to about 95° C., and the total pressure within the autoclave is maintained between about 60 kPa and about 3000 kPa, preferably about 350 kPa. The pressure within the autoclave can be maintained by using any suitable means such as a back pressure regulator.

Gaseous chlorinated hydrocarbon is then added to the autoclave at a rate that varies as a function of the amount of HF and tin catalyst within the autoclave, e.g., adding chlorinated hydrocarbon at a rate of about 10 to about 100 sccm (about 0.01 to about 0.5 kg/hr/kg-catalyst). A gaseous effluent exiting a reflux condenser, which is in fluid communication with the autoclave, is collected by condensation and monitored. The composition of the effluent is monitored by using an on-line gas chromatograph (GC). After the addition of chlorinated hydrocarbon has ceased, the autoclave is vented of excess gaseous and liquid materials by a nitrogen purge. The solid contents of the autoclave are then removed, drowned with water and filtered. The filtrate is rinsed with 10% aqueous hydrochloric acid, water, and dried in a vacuum oven to a constant weight. The composition of the dried mass is also analyzed in order to determine the amount of tar that is formed.

While the aforementioned batch process can be employed, a continuous process is particularly desirable from an industrial standpoint. Referring now to FIG. 1, FIG. 1 is a schematic diagram for a continuous HFC-152a manufacturing process. A reactor 1 is in fluid communication with a reflux column 2. Typically, the reflux column 2 will have a reflux ratio of between about 2 to about 20 when operated at a pressure of about 340 to about 3000 kPa and a temperature of about 50° to about 150° C. Predetermined amounts (ratios as previously discussed for batch process) of HF, at least one tin catalyst and at least one compound selected from the group consisting of metal and nonmetal alkoxides are added to the reactor 1. The contents of the reactor 1 are agitated by using a dual bladed agitator with pump down action 3, heated, and brought to reflux at the desired operating temperature/pressure. When the desired operating conditions have been established, HF and chloroethene are fed continuously to the reactor via one or more feed lines 4. Gas exits from the reactor 1 and is transported to the reflux column 2 via one or more feed lines 5. The gas stream leaving the reflux column 2 typically consists essentially of HFC-152a and HCl. A liquid return line 6 is connected to the bottom of the reflux column 2. Line 6 returns high boiling intermediates such as HCFC-151a and 1,1-dichloroethane, and any HF to reactor 1. The gas stream leaving the reactor 1 or reflux column 2 can be purified by any suitable manner such as by using two conventional distillation steps (not shown in FIG. 1). The first distillation step removes HCl. The second distillation step removes any unreacted intermediates and HF that are recovered and, if desired, recycled to reactor 1.

Similar to operating a batch process as discussed earlier, the continuous production equipment and its associated feed lines, effluent lines and any handling units should be constructed of materials resistant to HF and HCl.

While the previous description has placed particular emphasis upon making a product stream wherein a single fluorinated hydrocarbon is the major component, the inventive process can also be operated in a manner which co-produces other desirable compounds. For example, the inventive process can produce HFC-152a from chloroethene alone, or co-produce HFC-152a with one or more of 1,1-dichloro-1-fluoroethane (HCFC-141b), HCFC-142b, HFC-143a, among others, e.g., from a chlorinated hydrocarbon such as 1,1-dichloroethene. The co-produced product can be recovered and employed as a useful mixture, or separated into its individual components.

The following examples are provided for the purpose of further illustrating the present invention without limiting the invention as defined in the appended claims..). All compounds employed in the following examples were commercially available. For example, chloroethene was supplied by Fluka Incorporated, Ronkonkoma, N.Y. and HF was supplied by Air Products (Allentown, Pa.).

EXAMPLES

Example 1-Borate Additive in Preparation of HFC-152a From Chloroethene

Tin tetrachloride ($SnCl_4$, 37.5 g, 0.144 mole) was added to a Hastelloy C® 450 cc Parr® Series 4560 Mini Reactor in a dry box. The reactor head, which was equipped with a 0.25 inch diameter tube reflux condenser, was attached then the reactor removed from the drybox and connected to a stainless steel vacuum line. The base of the reactor was immersed in liquid nitrogen and HF (150 g, 7.5 mole) was vacuum transferred into the reactor. The liquid nitrogen cooling bath was removed and triethyl borate (B(OC$_2$H$_5$)$_3$, 6.35 g, 0.0435 mole) was charged to the reactor via syringe through a septum port. The temperature of the reactor was raised using external heating until the internal temperature was near 25° C., and cooling water (3.7 C) was begun circulating through the condenser. A heating jacket was placed around the reactor, and the internal temperature of the reactor was brought to 50° C. while maintaining the internal pressure at 350 kPa by use of a back pressure regulator. At this time, flow of chloroethene (49.2 sccm, 8.2×10$^{-7}$ m$^3$/sec) and internal standard methane (9.5 sccm, 1.6×10$^{-7}$ m$^3$/sec) were begun. The gaseous effluent was monitored every hour for the 16.5 hours of chloroethene addition. The molar yield of HFC-152a based on the chloroethene fed was measured to be 86%. The HFC-152a was measured by on-line gas chromatography (GC) to be 98% of the effluent. The ratio of HFC-152a/HCFC-151a (averaged from the 4$^{th}$ to the 16$^{th}$ hour of the experiment) measured by GC was 131. At the end of the run, the reactor was vented to atmospheric pressure to drive off volatiles (HF and organics). Further removal of volatiles was assisted by a nitrogen purge. The solids remaining in the autoclave were drowned in water and filtered on a Teflon® membrane filter. The filtrate was washed with 10% HCl and then with water and dried in a vacuum oven to constant weight.

The tars formed over this run averaged 1.00 g per 100 g chloroethene fed.

Example 2-Silicate Additive in Preparation of HFC-152a From Chloroethene

The apparatus, procedure, and materials used for this example were identical to those discussed for Example 1. The following discussion documents results obtained from this example and deviations in procedure from that in Example 1.

Tetraethyl orthosilicate (Si(OC$_2$H$_5$)$_4$, 9.61 g, 0.0461 mole) was used as the additive and was added with the SnCl$_4$. The molar yield of HFC-152a based on the chloroethene fed was 83%. The HFC-152a product was measured by on-line GC to be 98% of the effluent. The molar ratio of HFC-152a/HCFC-151a (averaged from the 4$^{th}$ to the 16$^{th}$ hour of the experiment) was measured by GC to be 53. After 16.5 hours of operation, the reaction was stopped and worked-up as in example 1. The tars formed over this run averaged 0.19 g per 100 g chloroethene fed.

Comparative Example 1-Preparation of HFC-152a from Chloroethene Using No Additive The apparatus, procedure, and materials used for this example were identical to those discussed for Example 1. The following discussion documents results obtained from this example and deviations in procedure from that in Example 1.

No alkoxide additive was used in this reaction. The HFC-152a product was measured by on-line GC to be 98% of the effluent. The molar ratio of HFC-152a/HCFC-151a (averaged from the 4$^{th}$ to the 17$^{th}$ hour of the experiment) was measured by GC to be 40. After 18 hours of operation, the reaction was stopped and worked-up as in example 1. The tars formed over this run averaged 2.30 g per 100 g chloroethene fed.

Example 3-Silicate Additive in Preparation of HFC-143a from 1,1-dichloroethene

The apparatus, procedure, and materials used for this example were identical to those discussed for Example 1. The following discussion documents results obtained from this example and deviations in procedure from that in Example 1.

Tetraethyl orthosilicate (Si(OC$_2$H$_5$)$_4$, 6.00 g, 0.029 mole) was charged to the reactor with the SnCl$_4$. The chlorinated hydrocarbon used was 1,1-dichloroethene (CH$_2$=CCl$_2$, 15.4 sccm, 2.6×10$^{-7}$ m$^3$/sec), with methane (10.3 sccm, 1.7×10$^{-7}$ m$^3$/sec) used as an internal standard. The gaseous effluent was monitored every hour for the 16.0 hours of 1,1-dichloroethene addition. The absolute yields of products HFC-143a, HCFC-142b, and 1,1,1-trichloroethane were 88.7%, 11.5%, and 0.1%, respectively, based on the 1,1-dichloroethene fed. The mole ratio of HFC143a/HCFC-142b (averaged from the 5$^{th}$ to the 16$^{th}$ hour of the experiment) measured by GC was 7.7. After 16 hours of operation, the reaction was stopped and worked-up as in Example 1. No measurable amount of tar was found to have formed.

Comparative Example 2-Preparation of HFC-143a from 1,1-Dichloroethene Using No Additive The apparatus, procedure, and materials used for this example were identical to those discussed for Example 3. The following discussion documents results obtained from this example and deviations in procedure from that in Example 3.

No alkoxide additive was used in this run. The gaseous effluent was monitored every hour for the 16 hours of 1,1-dichloroethene addition. The absolute molar yields of HFC-143a, HCFC-142b, and 1,1,1-trichloroethane were 59.3%, 36.7%, and 0.7%, respectively, based on the 1,1-dichloroethene fed. The mole ratio of HFC-143a/HCFC-142b (averaged from the 5$^{th}$ to the 16$^{th}$ hour of the experiment) measured by GC was 1.6. After 16 hours of operation, the reaction was stopped and worked-up as in example 1. No measurable amount of tar was found, but the filter membrane was orange in color indicating the formation of lower molecular weight oligomers.

Example 4-Preparation of HFC-143a From 1,1,1-Trichloroethane Using A Silicate Additive The apparatus, procedure, and materials used for this example were identical to those discussed for Example 1. The following discussion documents results obtained from this example and deviations in procedure from that in Example 1.

Tetraethyl orthosilicate (Si(OC$_2$H$_5$)$_4$, 6.00 g, 0.029 mole) was charged to the reactor with the SnCl$_4$. The chlorinated hydrocarbon used was 1,1,1-trichloroethane (CCl$_3$–CH$_3$, 12.3 sccm, 2.1×10$^{-7}$ m$^3$/sec), with methane (10.3 sccm, 1.7×10$^{-7}$ m$^3$/sec) used as an internal standard. The gaseous effluent was monitored every hour for the 14 hours of 1,1,1-trichloroethane addition. The absolute molar yields of HFC-143a, HCFC-142b, and 1,1,1-trichloroethane were 89.6%, 15.3%, and 0.0%, respectively, based on the 1,1,1-trichloroethane fed. The mole ratio of HFC-143a/HCFC-142b (averaged from the 5$^{th}$ to the 14$^{th}$ hour of the experiment) measured by GC was 5.9. After 14 hours of operation, the reaction was stopped and worked-up as in example 1. No measurable amount of tar was found to have formed.

Comparative Example 3-Preparation of HFC-143a from 1,1,1-Trichloroethane Using No Additive The apparatus, procedure, and materials used for this example were identical to those discussed for Example 4.

The following discussion documents results obtained from this example and deviations in procedure from that in Example 4.

No alkoxide additive was used in this run. The gaseous effluent was monitored every hour for the 16 hours of 1,1,1-trichloroethane addition. The absolute molar yields of HFC-143a, HCFC-142b, and 1,1,1-trichloroethane were 48.9%, 45.5%, and 0.8%, respectively, based on the 1,1,1-trichloroethane fed. The mole ratio of HFC-143a/HCFC-142b (averaged from the $5^{th}$ to the $16^{th}$ hour of the experiment) measured by GC was 1.1. After 14 hours of operation, the reaction was stopped and worked-up as in Example 1. No measurable amount of tar was found to have formed.

Example 5-Coproduction of HFC-143a (from 1,1-Dichloroethene) with HFC-152a from (Chloroethene) Using a Silicate Additive The apparatus, procedure, and materials used for this example were identical to those discussed for Example 1. The following discussion documents results obtained from this example and deviations in procedure from that in Example 1.

Tetraethyl orthosilicate ($Si(OC_2H_5)_4$, 6.00 g, 0.029 mole) was charged to the reactor with the $SnCl_4$. Two chlorinated hydrocarbons were co-fed to the reactor; 1,1-dichloroethene ($CH_2=CCl_2$, 10.5 sccm, $1.75 \times 10^{-7}$ m$^3$/sec) and chloroethene (25.3 sccm, $4.23 \times 10^{-7}$ m$^3$/sec), with methane (10.3 sccm, $1.7 \times 10^{-7}$ m$^3$/sec) used as an internal standard. The gaseous effluent was monitored every hour for the 13 hours of chlorinated hydrocarbon co-addition. The molar yields of HFC-143a (based on 1,1-dichloroethene), HCFC-142b (based on 1,1-dichloroethene), and HFC-152a (based on chloroethene) were 79.4%, 15.9%, and 100%, respectively. The mole ratio of HFC-143a/HCFC-142b (averaged from the 5 th to the 14 th hour of the experiment) was measured by GC to be 5.0, and the ratio of HFC-152a/HCFC-151a was measured by GC to be 51. After 13 hours of operation, the reaction was stopped and worked up as in example 1. The tars formed over this run averaged 0.05 g per 100 g of chlorinated hydrocarbon fed.

What is claimed is:

1. A process for the manufacture of fluorinated hydrocarbon comprising:
   a) providing a first liquid phase mixture comprising: at least one chlorinated hydrocarbon selected from the group consisting of the formula $R^1R^2C=CR^3R^4$ and $CR^5R^6R^7R^8$, wherein at least one of $R^1$ through $R^4$ in $R^1R^2C=CR^3R^4$, and at least one of $R^5$ through $R^8$ in $CR^5R^6R^7R^8$ is chlorine, and wherein the remainder of $R^1$ through $R^4$ in $R^1R^2C=CR^3R^4$, and $R^5$ through $R^8$ in $CR^5R^6R^7R^8$ are identical or different and are selected from the group consisting of H, F, Cl, Br, and $C_{(y)}Z_{(2y+1)}$, wherein Z is identical or different and is selected from the group consisting of H, F, Cl and Br, and y is an integer from 1 to 6,
   hydrogen fluoride,
   at least one tin catalyst, and
   at least one additive selected from the group consisting of a metal alkoxide and a nonmetal alkoxide represented by $M(OR^9)_x$, wherein M is selected from the group of elements consisting of Li, Na, K, Rb, Cs, Be, Mg, Ca, Sr, Ba, Ti, B, Al, Si, Ge, Sn, and Pb, $R^9$ is selected from the group consisting of $C_1$ through $C_6$ alkyl, and x is from 1 to 4;
   b) heating said first mixture, and;
   c) recovering a second mixture comprising fluorinated hydrocarbon wherein said second mixture is substantially free of oligomeric and polymeric compounds.

2. A process for the manufacture of fluorinated hydrocarbon comprising:
   a) providing a first liquid phase mixture comprising:
      at least one chlorinated hydrocarbon selected from the group consisting of $CH_2=CHCl$, $CH_2=CCl_2$, $CCl_2=CCl_2$, $CCl_3$—$CH_3$, $CHCl_2$—$CH_2Cl$, and $CCl_3$—$CH_2$—$CCl_3$,
      hydrogen fluoride,
      at least one tin catalyst selected from the group consisting of $SnCl_4$, $SnCl_3F$, $SnCl_2F_2$, $SnClF_3$, and $SnF_4$, and
      at least one additive selected from the group consisting of a boron and silicon alkoxide represented by $B(OR)_3$ and $Si(OR)_4$, wherein R may be identical or different and is selected from the group consisting of $C_1$ through $C_6$ alkyl;
   b) heating said first mixture, and;
   c) recovering a second mixture comprising fluorinated hydrocarbon wherein said second mixture is substantially free of oligomeric and polymeric compounds.

3. The process of claim 1 wherein said chlorinated hydrocarbon is selected from the group consisting of $CH_2=CHCl$, $CH_2=CCl_2$, $CCl_2=CCl_2$, $CCl_3$—$CH_3$, $CHCl_2$—$CH_2Cl$, $CCl_3$—$CH_2$—$CCl_3$, $CHClF$—$CH_3$, $CClF_2$—$CH_3$, $CFCl_2$—$CH_3$, $CHCl_2$—$CCl_2F$, $CHCl_2$—$CClF_2$, $CHCl_2$—$CF_3$, $CHClF$—$CClF_2$, $CHClF$—$CClH_2$, $CHCl_2$—$CFH_2$, $CHF_2$—$CClH_2$, $CHFCl$—$CFH_2$, $CCl_3$—$CH_2$—$CCl_2F$, $CCl_3$—$CH_2$—$CClF_2$, $CCl_3$—$CH_2$—$CF_3$, $CCl_2F$—$CH_2$—$CF_3$, $CClF_2$—$CH_2$—$CF_3$, $CCl_2F$—$CH_2$—$CCl_2F$, $CCl_2F$—$CH_2$—$CClF_2$, and $CClF_2$—$CH_2$—$CClF_2$.

4. The process of claim 1 or 2 wherein said fluorinated hydrocarbon is at least one compound selected from the group consisting of $CHF_2$—$CH_3$, $ClCHF$—$CH_3$, $CF_3$—$CH_3$, $CClF_2$—$CH_3$, $CCl_2F$—$CH_3$, $CHCl_2$—$CCl_2F$, $CHCl_2$—$CClF_2$, $CHClF$—$CCl_2F$, $CHCl_2$—$CF_3$, $CHClF$—$CClH_2$, $CHCl_2$—$CFH_2$, $CHF_2$—$CClH_2$, $CHFCl$—$CFH_2$, $CHF_2$—$CFH_2$, $CCl_3$—$CH_2$—$CCl_2F$, $CCl_3$—$CH_2$—$CClF_2$, $CCl_3$—$CH_2$—$CF_3$, $CCl_2F$—$CH_2$—$CF_3$, $CClF_2$—$CH_2$—$CF_3$, $CF_3$—$CH_2$—$CF_3$, $CCl_2F$—$CH_2$—$CCl_2F$, $CCl_2F$—$CH_2$—$CClF_2$, and $CClF_2$—$CH_2$—$CClF_2$.

5. The process of claim 1 wherein said tin catalyst comprises at least one member from the group consisting of $SnCl_4$, $SnBr_4$, $SnCl_3F$, $SnCl_2F_2$, $SnClF_3$, $SnF_4$, $SnCl_2O$, $SnF_2O$, $SnClFO$, $Sn(CH_3)_4$, $OSn(C_2H_5)_2$, and $SnCl_2(CH_3)_2$.

6. The process of claim 1 or 2 wherein said heating is carried out at a temperature in the range of about 20° C. to 160° C.

7. The process of claim 6 wherein said heating is carried out at a temperature in the range of about 50° C. to about 95° C.

8. The process of claim 1 or 2 wherein the mole ratio of said additive to said tin catalyst is is from about 0.25 to 1.

9. The process of claim 1 or 2 wherein the weight of said tin catalyst is from about 5% to about 35% the weight of hydrogen fluoride.

10. The process of claim 1 or 2 wherein said process is continuous process.

* * * * *